United States Patent [19]
Paul et al.

[11] Patent Number: 5,208,333
[45] Date of Patent: May 4, 1993

[54] (2R)-1-(ARYLOXY)-3-(BUTYRYLOXY)-2-PROPANOLS

[75] Inventors: Axel Paul, Mannheim; Wolfgang Ladner, Fussgoenheim; Hardo Siegel, Speyer, all of Fed. Rep. of Germany

[73] Assignee: BASF Aktiengesellschaft, Ludwigshafen, Fed. Rep. of Germany

[21] Appl. No.: 282,000

[22] Filed: Dec. 9, 1988

[30] Foreign Application Priority Data

Dec. 12, 1987 [DE] Fed. Rep. of Germany ....... 3742222

[51] Int. Cl.$^5$ ............................................. C07D 295/24
[52] U.S. Cl. ..................................... 544/134; 544/302; 544/408; 546/157; 546/301; 548/122; 548/229; 548/243; 548/255; 548/268.6; 548/444; 548/484; 548/264.4; 549/66; 549/475; 560/254; 560/255
[58] Field of Search ................. 560/254, 255; 544/134

[56] References Cited

U.S. PATENT DOCUMENTS 3,803,216   4/1974   Larsen et al. ........................ 560/254

FOREIGN PATENT DOCUMENTS 0008973   3/1980   European Pat. Off. ............. 560/254

OTHER PUBLICATIONS

Chemical & Engineering News, Jun. 1986, p. 24.
J. Am. Chem. Soc., vol. 106 (1984), pp. 7250–7251.

*Primary Examiner*—Mary C. Lee
*Assistant Examiner*—Jacqueline Haley
*Attorney, Agent, or Firm*—Herbert B. Keil

[57] ABSTRACT

(2R)-1-(Aryloxy)-3-(butyryloxy)-2-propanols of the general formula (I), where Ar is a monocyclic or polycyclic aromatic or heteroaromatic radical, and a process for their preparation by the reaction of (2R)-glycidyl butyrate with an aromatic hydroxy compound Ar—OH in the presence of a quaternary ammonium halide.

4 Claims, No Drawings

(2R)-1-(ARYLOXY)-3-(BUTYRYLOXY)-2-PROPANOLS

The present invention relates to (2R)-1-(aryloxy)-3-(butyryloxy)-2-propanols of the general formula (I),

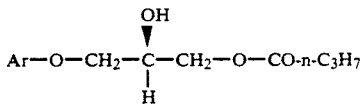

where Ar is a monocyclic or polycyclic aromatic or heteroaromatic radical, and a process for their preparation.

The preparation of (2S)-propranolol, the drug for treating cardiac and circulatory disorders, from (2R)-glycidol and 1-naphthol via (2R)-3-(1-naphthyloxy)-1,2-propanediol is known from Chem. Eng. News, (June), 24 (1986), and the scheme is shown below. However, this process suffers from the drawback that the optically active (2R)-glycidol is difficultly accessible and correspondingly expensive.

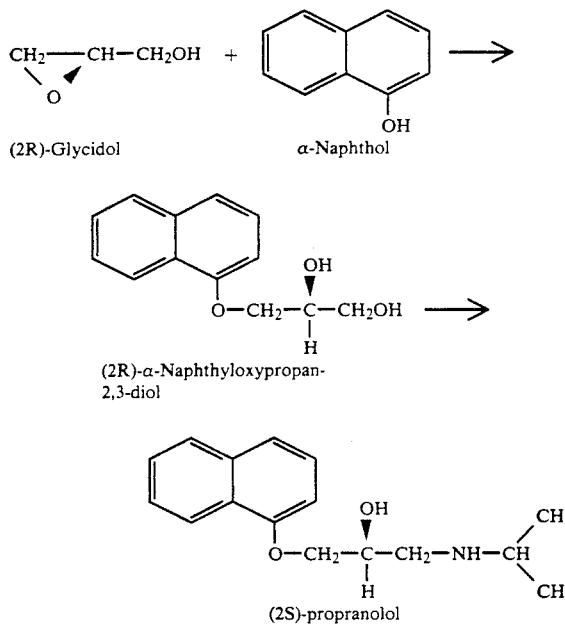

It is also known however—from J. Am. Chem. Soc., 106, 7250-1(1984)—that (2R)-glycidyl butyrate (II)

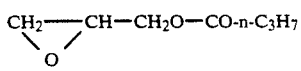

can be obtained relatively simply by an enzymatic method, hence the general aim of the present invention was to make (2S)-propranolol—and similar compounds whose molecules include the structure (I')—

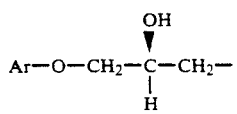

accessible in a more economic way starting from the glycidyl ester (II). Particular aims were to find novel intermediates suitable for the synthesis of (2S)-propranolol and similar drugs and a process for the preparation of such intermediates.

Accordingly we have found (2R)-1-(Aryloxy)-3-(butyryloxy)-2-propanols of the general formula (I) given above. We have also found that these compounds are obtained by the reaction of (2R)-glycidyl butyrate (II) with aromatic hydroxy compounds Ar—OH in the presence of a quaternary ammonium halide.

Practically any quaternary ammonium halide is suitable as a catalyst for the reaction between the glycidyl ester (II) and the aromatic hydroxy compound, but iodides are most suitable, followed by bromides and chlorides. Salts of the general formula (IIIa)

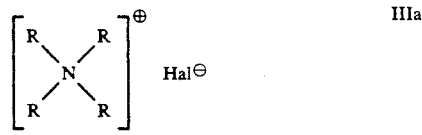

are preferred, where either all the radicals R are identical or different alkyls of from 1 to 4 carbon atoms or three of the radicals R are identical or different alkyls of from 1 to 4 carbon atoms and one is either an alkyl of from 5 to 18 carbon atoms or benzyl, and Hal is chloride, bromide, or iodide. Examples are benzyltrimethylammonium chloride and bromide, tetramethylammonium chloride and iodide, and, above all, tetrabutylammonium bromide and iodide.

The proportion of these catalysts is not critical, but to achieve economically satisfactory rates of reaction the mole ratio of catalyst to aromatic hydroxy compound is from 0.5% to 20% as a rule.

Preferably equal amounts of glycidyl ester (II) and the aromatic hydroxy compound are allowed to react, but if the latter is very unreactive it can be advantageous to employ an excess of one reactant, say up to 50% excess.

The recommended range of reaction temperatures is from 50° C. to 150° C. Lower temperatures, say down to 0° C., would normally be used only for very sensitive aromatic hydroxy compounds, and at higher temperatures, especially above 160° C., side reactions such as the racemization of the product (I) and both the racemization and polymerization of the glycidyl ester (II) are likely.

As a rule the reaction is conducted under atmospheric pressure or, if a volatile solvent or diluent is used, under the slightly higher vapor pressure of the reaction mixture.

Generally it is advantageous in practice to add a solvent or diluent, although this is not necessary in principle.

Suitable solvents—or diluents, if the reaction is to be carried out in suspension—are inert organic liquids: halogenated hydrocarbons, such as methylene chloride; ethers, such as diethyl ether or tetrahydrofuran; ketones, such as acetone; esters, such as ethyl or butyl acetate; aromatic hydrocarbons, such as toluene. The mass ratio of solvent to aromatic hydroxy compound is generally from 1:1 to 6:1.

The novel process has no technical peculiarities, so it is not necessary to describe it in greater detail. The same applies to subsequent treatment of the reaction mixture.

The success of the novel process has not been found to depend on the nature of the aromatic or heteroaromatic radical Ar, provided it does not carry reactive substituents such as carboxyl, sulfo, mercapto, hydroxy, amino, or secondary amino groups. Possible aromatic or heteroaromatic radicals Ar include phenyl, pyrazinyl, and all possible naphthyls, pyridyls, pyrimidinyls, triazolyls, quinolyls, oxazolyls, isoxazolyls, thiaoxazolyls, thiadioxazolyls, indolyls, carbazolyls, furyls, and thienyls.

The aromatic or heteroaromatic radical Ar may carry one or more inert substituents, for instance: alkyl, alkoxy, alkoxycarbonyl, acyloxy, or acyl radicals of up to 4 carbon atoms and the corresponding radicals containing olefinic or acetylenic unsaturation; cycloalkyl and cycloalkenyl radicals of from 3 to 7 ring carbon atoms; arylalkyl or arylalkenyl radicals, such as benzyl, 1-phenylethyl, 2-phenylethyl, 1-phenylethenyl, and 2-phenylethenyl; aryls, such as phenyl; halogeno radicals, such as fluoro, chloro, and bromo; halogenoalkyls, such as trifluoromethyl; dialkylamino radicals with a total of from 2 to 6 carbon atoms; cyano; nitro.

When the aromatic or heteroaromatic radical Ar is 1-naphthyl the novel process and corresponding intermediate (I) are particularly important, because of their relevance to the preparation of a known drug—(S)-propranolol. The same applies when Ar is 4-morpholino-1,2,5-thiadiazol-3-yl or 2-cyclopentylphenyl, as in the aromatic hydroxy compounds

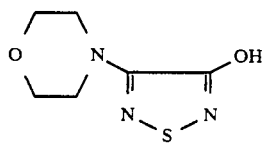

3-hydroxy-4-morpholino-1,2,5-thiadiazole and

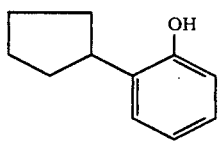

2-cyclopentylphenol, from which the known drugs timolol and penbutolol can be derived.

In general the novel process and corresponding novel intermediates (I) widen the possibility of economically synthesizing many compounds whose molecules include the structure (I'), which belong to an important group of drugs.

As a rule the butyryloxy group in the intermediates (I) is subsequently hydrolyzed by known methods, giving the corresponding substituted propanediols, which are then subjected to further reactions.

EXAMPLE 1

Preparation of (2R)-1-(butyryloxy)-3-(1-naphthyloxy)-2-propanol

To a solution of 144 g (1 mol) of 1-naphthol and 7.4 g (0.02 mol) of tetrabutylammonium iodide in 200 ml of toluene was added 144 g (1 mol) of (R)-glycidyl butyrate over a period of 15 min at a temperature of 120° C., and the mixture was kept at this temperature for a further 4 h. Conventional subsequent treatment of the reaction mixture gave the required compound as an oil, yield about 75%.

NMR (CDCl$_3$) t 0.92 (3H), J=7; sextet 1.65 (2H), J=7; t 2.33 (2H), (J=7; m 4.20 (2H); m 4.30 (3H); d 6.78 (1H), J=7; dd 7.34 (1H), J=7+7; m 7.4 (4H); m 7.8 (1H); m 8.2 (1H).

EXAMPLE 2

Preparation of (2R)-1-(butyryloxy)-3-(2-cyclopentylphenoxy)-2-propanol

In the manner described in Example 1 this compound was prepared from 162 g (1 mol) of 2-cyclopentylphenol and the amounts of other reactants given in Example 1. The required compound was obtained as an oil, yield 72%.

NMR (CDCl$_3$) t 0.95 (3H), J=7; sextet 1.67 (2H), J=7; m 1.7 (6H); m 2.0 (2H); t 2.38 (2H), J=7; 2.73 sbr. (1H); quintet 3.33 (1H), J=7; m 4.085 (2H); m 4.30 (3H); d 6.83 (1H), J=7; t 6.95 (1H), J=7; t 7.16 (1H), J=7; d 7.23 (1H), J=7.

We claim:

1. A (2R)-1-(aryloxy)-3-(butyryloxy)-2-propanol of the formula (I),

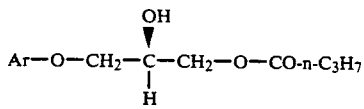

in which Ar denotes phenyl, pyrazinyl, 1-naphthyl, 2-naphthyl, pyridyl, pyrimidyl, triazolyl, quinolyl, oxazolyl, isoxazolyl, thiaoxazolyl, thiadioxazolyl, indolyl, carbazolyl, furyl and thienyl or the foregoing radicals bearing the following substituents: alkyl, alkenyl, alkynyl, alkoxy, alkenoxy, alkynoxy, alkoxycarbonyl, alkenoxycarbonyl, alkynoxycarbonyl, acyloxy or acyl radicals of up to 4 carbon atoms, or cycloalkyl or cycloalkenyl radicals of from 3 to 7 ring carbon atoms, or benzyl, 1-phenylethyl, 2-phenylethyl, 1-phenylethenyl, 2-phenylethenyl, phenyl, fluoro, chloro, bromo, or halogenoalkyl or dialkylamino radicals with a total of 2 to 6 carbon atoms, or cyano or nitro.

2. 1-(Butyryloxy)-3-(1-naphthyloxy)-2-propanol.

3. (2R)-1-(butyryloxy)-3-[(4-morpholino-1,2,5-thiadiazol-3-yl)oxy]-2-propanol.

4. (2R)-1-(Butyryloxy)-3-(2-cyclopentylphenoxy)-2-propanol.

* * * * *